United States Patent
Wilke et al.

(10) Patent No.: US 10,724,989 B2
(45) Date of Patent: Jul. 28, 2020

(54) AMPEROMETRIC CHLORINE DIOXIDE SENSOR

(71) Applicant: Endress+Hauser Conducta GmbH+Co. KG, Gerlingen (DE)

(72) Inventors: Stefan Wilke, Halle (DE); Magdalena Losik-Strassberger, Gohrisch (DE); Erik Hennings, Freiberg (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 78 days.

(21) Appl. No.: 16/031,005

(22) Filed: Jul. 10, 2018

(65) Prior Publication Data

US 2019/0011399 A1  Jan. 10, 2019

(30) Foreign Application Priority Data

Jul. 10, 2017 (DE) ........................ 10 2017 115 421

(51) Int. Cl.
*G01N 27/404* (2006.01)
*G01N 27/49* (2006.01)
(Continued)

(52) U.S. Cl.
CPC ............. *G01N 27/49* (2013.01); *G01N 27/30* (2013.01); *G01N 27/4035* (2013.01); *G01N 33/1886* (2013.01)

(58) Field of Classification Search
CPC .. G01N 27/333; G01N 27/4035; G01N 27/30; G01N 33/1826
See application file for complete search history.

(56) References Cited

U.S. PATENT DOCUMENTS 4,176,032 A   11/1979  Stevenson, Jr.
4,441,979 A    4/1984  Dailey
(Continued)

FOREIGN PATENT DOCUMENTS

DE    10322894 A1    12/2004

OTHER PUBLICATIONS

Sensorex Product Instruction Sheet for Chlorine Dioxide Amperometric 4-20mA Sensors, 2011, six pages (Year: 2011).*
(Continued)

*Primary Examiner* — Alexander S Noguerola
(74) *Attorney, Agent, or Firm* — Kelly J. Smith; PatServe

(57) ABSTRACT

The present disclosure relates to an amperometric sensor for determining measurement values of a measurand representing a chlorine dioxide content of a measuring fluid, the sensor including a sensor housing in which a housing chamber is formed, a membrane sealing the housing chamber, a working electrode arranged within the housing chamber, a counter electrode arranged within the housing chamber, an inner electrolyte contained in the housing chamber and in contact with the membrane, the working electrode and the counter electrode, the inner electrolyte having a pH value between 3.5 and 9, inclusive, and a pH buffer stabilizing the inner electrolyte. The sensor further includes a measurement circuit electrically connected with the working electrode and the counter electrode and configured to apply a predetermined, constant voltage between the working electrode and the counter electrode and to generate at least one measurement signal representing a measurement value of the measurand.

7 Claims, 2 Drawing Sheets

(51) Int. Cl.
    *G01N 33/18*     (2006.01)
    *G01N 27/403*     (2006.01)
    *G01N 27/30*     (2006.01)

(56) References Cited

U.S. PATENT DOCUMENTS

| | | |
|---|---|---|
| 5,624,546 A | 4/1997 | Milco |
| 2005/0011771 A1* | 1/2005 | Wittkampf ......... G01N 27/4168 205/778.5 |

OTHER PUBLICATIONS

Sensorex Safety Data Sheet for product CLDA-5015, 2011, six pages (Year: 2011).*

Persat et al., "Basic principles of electrolyte chemistry for microfluidic electrokinetics. Part I: Acid-base equilibria and pH buffers," Lab Chip, 2009, 9, 2437-2453 (Year: 2009).*

Online article entitled Preparation of pH buffer solutions by Dhanlal De Lloyd, downloaded on Nov. 22, 2019 from http://delloyd.50megs.com/moreinfo/buffers2.html#phosphate (Year: 2000).*

Kushner-Lenhoff et al., "Effects of aqueous buffers on electrocatalytic oxidation with an iridium oxide material electrodeposited in thin layers from an organometallic precursor," Dalton Trans., 2013, 42, 3617-3622 (Year: 2013).*

Search Report for German Patent Application No. 10 2017 115 421.3, German Patent Office, dated Apr. 25, 2018, 6 pp.

\* cited by examiner

AMPEROMETRIC CHLORINE DIOXIDE SENSOR

CROSS-REFERENCE TO RELATED APPLICATION

The present application is related to and claims the priority benefit of German Patent Application No. 10 2017 115 421.3, filed on Jul. 10, 2017, the entire contents of which are incorporated herein by reference.

TECHNICAL FIELD

The present disclosure relates to an amperometric sensor for determining measurement values of a measurand representing a chlorine dioxide content of a measuring fluid.

BACKGROUND

Chlorine dioxide ($ClO_2$) is used in the preparation of service water, for example of drinking water, or in swimming pools for disinfection, i.e., for killing pathogens. The chlorine dioxide concentration is monitored and controlled or regulated in order to dose the chlorine dioxide used, and/or to monitor the water quality. For example, sensors that operate according to the amperometric measurement principle may be used for this purpose.

Amperometric sensors that are available today for determining a chlorine dioxide concentration or a value correlated therewith, for example a chlorine dioxide activity or a chlorine dioxide partial pressure, normally comprise a measurement probe that can be immersed into a measuring fluid, which measurement probe can be connected with superordinate sensor electronics, for example a measuring transducer or other electronics for measurement value processing. The measurement probe of these sensors comprises a probe housing in which is formed a housing chamber sealed by a membrane and filled with an inner electrolyte. The membrane is arranged within a region of the measurement probe designated for contact with the measuring fluid and is permeable, in particular selectively permeable to chlorine dioxide, such that chlorine dioxide may get from the measuring fluid into the housing chamber and vice versa.

At least two electrodes contacting the inner electrolyte are arranged within the housing chamber. In some embodiments, three electrodes may also be present. The electrodes are connected in an electrically conductive manner with the measurement circuit arranged outside of the housing chamber, which measurement circuit may be a component of on-site electronics arranged in the probe housing, for example. One of the electrodes is used as working electrode, another as counter electrode. To determine the measurand, a predetermined voltage is applied by means of the measurement circuit between the working electrode and the counter electrode, wherein the working electrode is connected as a cathode and the counter electrode is connected as an anode, so that chlorine dioxide contained in the inner electrolyte is electrochemically converted at the cathode. The current flowing through the inner electrolyte between the working electrode and the counter electrode is detected by means of the measurement circuit as a measure of the chlorine dioxide content in the measuring fluid. Given a measuring gas, the chlorine dioxide content may be indicated as a partial pressure; given a measuring liquid, the chlorine dioxide content may be indicated as a concentration. In applications with three electrodes, the potential of the working electrode or the current flow through the working electrode may be regulated by means of a third reference electrode through which current does not flow.

The inner electrolyte of these commercially available sensors is typically in the acidic or neutral pH range. However, it has surprisingly been shown that these conventional chlorine dioxide sensors can deliver incorrect measurement results given use in acidic measuring fluids.

From U.S. Pat. No. 4,176,032, a chlorine dioxide sensor is known that has a working electrode made of gold or platinum and a counter electrode made of silver or copper. In the absence of chlorine dioxide, the working electrode is negatively polarized and the counter electrode is positively charged, whereas in the presence of chlorine dioxide in the inner electrolyte, a reaction occurs at the working electrode, which reaction partially depolarizes the working electrode so that the working electrode may take up released electrons given an oxidation taking place at the counter electrode. This leads to a current flow that serves as a measurement signal and is linearly dependent on the chlorine dioxide concentration in the inner electrolyte. The inner electrolyte is an aqueous solution of a halide salt that additionally contains a complexing agent, for example EDTA, which complexes copper or silver ions that are formed in the oxidation reaction occurring at the counter electrode. The inner electrolyte may additionally contain a pH buffer. The complexing of the copper or silver ions passing into solution prevents a passivating copper oxide or silver oxide layer from forming at the counter electrode. Given that a sufficient concentration of the complexing agent in the inner electrolyte must be ensured in this sensor, the selection of the pH value of the inner electrolyte is possibly limited. U.S. Pat. No. 4,176,032 specifies EDTA as a suitable complexing agent. However, EDTA has a sufficient solubility only at high pH values, meaning in the basic pH range. Given low pH values, the EDTA concentration that is present in solution in the inner electrolyte may no longer be sufficient to prevent a negative effect on the sensor function. Complexing agents suitable for low pH values are not specified in U.S. Pat. No. 4,176,032.

SUMMARY

The present disclosure is based on the object of specifying an amperometric chlorine dioxide sensor that does not exhibit the disadvantages of the prior art. In particular, the amperometric chlorine dioxide sensor should also be stably operable in acidic measuring fluids over a long time period.

This object is achieved by the amperometric chlorine dioxide sensor according to claim 1. Advantageous embodiments are listed in the dependent claims.

The amperometric sensor according to the present disclosure for the determination of measurement values of a measurand representing a chlorine dioxide content of a measuring fluid, for example of a chlorine dioxide partial pressure, a chlorine dioxide concentration or a chlorine dioxide activity, comprises: a sensor housing in which a housing chamber is formed; a membrane sealing the housing chamber; a working electrode arranged within the housing chamber; a counter electrode arranged within the housing chamber; an inner electrolyte contained in the housing chamber and in contact with the membrane, the working electrode and the counter electrode, wherein the inner electrolyte has a pH value between 3.5 and 9, inclusive, and comprises a pH buffer stabilizing the pH value of the inner electrolyte; and a measurement circuit electrically connected with the working electrode and the counter electrode, which measurement circuit is designed to apply a predetermined, constant voltage between the working electrode and the counter electrode, and to generate at least one measurement signal representing a measurement value of the measurand using a current flowing through the inner electrolyte between the working electrode and the counter electrode given the predetermined voltage.

It has been shown that a higher reliability of the measurement values provided by the sensor is ensured in that the inner electrolyte has a pH value in a pH range of 3.5 to 9, inclusive, and comprises a pH buffer that serves to keep the pH value stable in this range.

It could be determined that, given a neutral or nearly neutral pH value, chlorine dioxide is reduced to chlorite ($ClO_2$—) at the working electrode connected as a cathode, whereas given an acidic pH value, in particular pH values below 3.5, chlorine dioxide is reduced to chloride (Cl—) at the cathode in multiple successive reaction steps. If, during operation of the sensor, the pH value of the inner electrolyte thus drops from a neutral value to an acidic pH value, in particular below 3.5, multiple findings are suggested by the correspondingly higher electron transfer at the cathode and by additional reactions proceeding in the acidic pH range in the inner electrolyte in which chlorine is formed, among other things. The response time of the sensor may simultaneously be lengthened. For example, a change of the pH value of the inner electrolyte may occur if hydronium ions get from the measuring fluid into the inner electrolyte via the membrane or leaks of the probe housing. If the measuring fluid comprises hydrochloric acid, gaseous hydrogen chloride may get into the inner electrolyte via the membrane and as a result lead to the dropping of the pH value of the inner electrolyte. By contrast, if a pH buffer is contained in the inner electrolyte, the pH value of the inner electrolyte may be kept stable at the initial pH value so that the described measurement errors do not occur even given operation of the sensor in an acid, in particular hydrochloric acid, measuring fluid.

The embodiment of the measurement circuit in the manner that a predetermined, constant voltage is applied between the working electrode and the counter electrode in order to detect measurement values is additionally advantageous because this prevents unwanted reactions at the working electrode and/or the counter electrode. The inner electrolyte therefore also does not need to contain a complexing agent, for example EDTA, in order to complex ions formed via oxidation at the counter electrode and keep them in solution in this way. This also enables the adjustment of a pH value selected from a wide pH value range in the inner electrolyte.

In one embodiment, the working electrode comprises a metal, in particular a noble metal such as gold or platinum. The counter electrode may be designed as a silver electrode which has a layer made of a silver halide, for example silver chloride.

The inner electrolyte preferably has a pH value in the range of 5 to 8, wherein the contained pH buffer accordingly has a buffering effect adapted to the pH value of the inner electrolyte, thus likewise in the pH range of 5 to 8.

An inner electrolyte that has a pH value of 7 and that comprises as a pH buffer a non-oxidizable, in particular inorganic, buffer buffering in the neutral pH range has proven to be very advantageous. For example, a phosphate buffer comes into consideration.

The inner electrolyte may be an aqueous solution that, in addition to the pH buffer, comprises at least one electrolyte salt, for example potassium chloride or a different alkali halide salt.

The membrane preferably has hydrophobic or super-hydrophobic properties and is permeable to chlorine dioxide. The membrane is advantageously impermeable to water. For example, such a membrane is a polymer membrane that has a plurality of pores that are permeable to gaseous chlorine dioxide, wherein the surface of the polymer membrane, in particular the inner surfaces of the pores, is hydrophobic or super-hydrophobic. Suitable membranes are, for example, super-hydrophobic polyvinylidene fluoride (PVDF) membranes or super-hydrophobic polytetrafluoroethylene (PTFE) membranes comprising pores.

BRIEF DESCRIPTION OF THE DRAWINGS

The present disclosure is explained in further detail below on the basis of the exemplary embodiments shown in the figures. Shown are.

DETAILED DESCRIPTION

Figure 1:
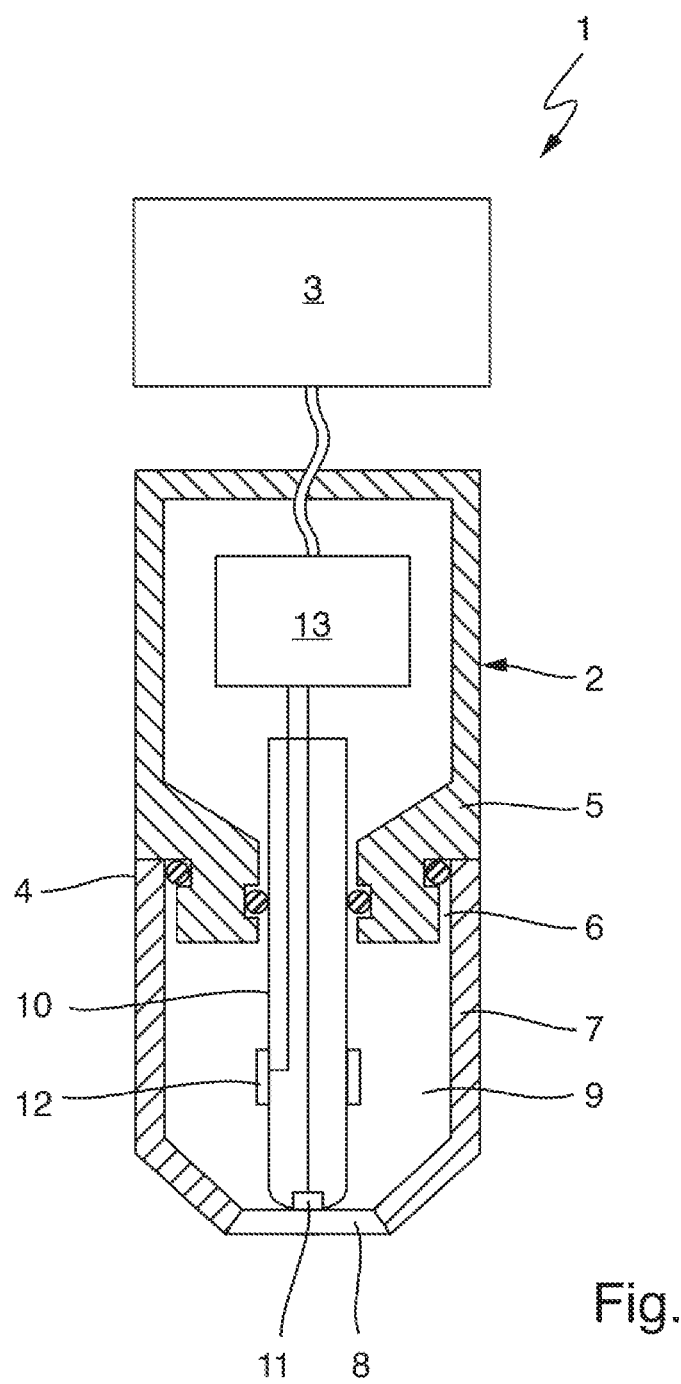
FIG. 1 shows a schematic, longitudinal section presentation of an amperometric chlorine dioxide sensor.

Schematically shown in FIG. 1 is an amperometric sensor 1 for determining a concentration of chlorine dioxide in a measuring fluid. The measuring fluid may be a gas mixture containing chlorine dioxide or a liquid in which chlorine dioxide is present in solution.

The sensor 1 comprises an essentially cylindrical measurement probe 2 and superordinate sensor electronics 3 connected with the measurement probe for communication, which sensor electronics 3 may be a measuring transducer in the present example. Instead of a measuring transducer, a different data processing device may also be the sensor electronics 3, for example a computer, a process control computer, a programmable logic controller, or even a control device set up for wireless communication, for example a tablet, a smartphone, a smartwatch, or data glasses.

The measurement probe 2 comprises a probe housing 4 that, in the example shown here, is made up of two parts, namely a probe body 5 and a sensor cap 7 that is connected by means of a screw connection 6 with the probe body 5 so as to be detachable. In the present example, the probe housing 4 consists of stainless steel but may also be formed from an electrically non-conductive material, for example a polymer material, such as polyether ether ketone (PEEK), PTFE or PVDF. The sensor cap 7 has an essentially cylindrical cap base body that is sealed by a membrane 8 at its end facing away from the screw connection 6, which end is designated for immersion into the measuring fluid. The membrane 8 is firmly connected with the cap base body, for example via a material connection, such as a glued or welded connection, or via a positive connection, such as a clamped connection.

The sensor cap 7 and the probe body 5 include a housing chamber 9 that, in the present example, is filled with an aqueous electrolyte solution serving as inner electrolyte. On the back side, meaning on its side facing away from the membrane 8, the housing chamber 9 is terminated in a liquid-tight manner by means of two seals so that the inner electrolyte does not get into the probe body 5 and also cannot exit out of the probe housing 4 via the screw connection 6.

The membrane 8 is formed from a plastic, for example silicone, PTFE or PVDF, and has a plurality of pores through which gaseous chlorine dioxide located in the measuring fluid can diffuse into the housing chamber 9. A diffusion in the reverse direction is also possible. In the equilibrium state, the concentration of chlorine dioxide in the inner electrolyte thus correlates with a chlorine dioxide content of the measuring fluid.

In an advantageous embodiment, the surface of the membrane 8, including the inner surfaces of the pores, may be designed to be super-hydrophobic. Super-hydrophobicity of a membrane surface, for example of a PVDF membrane surface, may be achieved via a surface treatment. The membrane 8 formed from PVDF is mechanically stable at a thickness between 1 and 200 μm even without an additional supporting structure. Due to the super-hydrophobicity of the membrane 8, penetration of water and other components dissolved in water through the membrane 8 into the housing chamber 9 and the inner electrolyte contained therein, or in the reverse direction, is avoided in principle. However, the membrane 8 may naturally also consist of conventional membrane materials, for example of silicone or PTFE.

The measurement probe 2 further comprises a rod-shaped electrode body 10 that is attached at the rear side of the probe body 5 and whose forward segment facing toward the membrane 8 is arranged in the housing chamber 9. In the present example, the electrode body 10 consists of an electrically non-conductive material, for example a polymer material, such as PEEK, PTFE or PVDF, or of glass. Embedded in the electrode body 10 is a first electrode that is referred to in the following as a working electrode 11 and that is exposed on the face of the electrode body 10 situated opposite the membrane 8 such that the working electrode 11 is in contact with the inner electrolyte. Moreover, the working electrode 11 is electrically insulated from the inner electrolyte by the electrode body 10. The working electrode 11 may be formed from a noble metal, for example gold or platinum, at least at its exposed end. Moreover, on the electrode body 11, an annular or sleeve-shaped second electrode, referred to in the following as a counter electrode 12, is placed in a region that is wetted by the inner electrolyte. For example, this counter electrode 12 may be formed from silver provided with a silver chloride coating. Both the working electrode 11 and the counter electrode 12 are connected in an electrically conductive manner with a measurement circuit 13 arranged within the probe body. The measurement circuit 13 is designed to apply a predetermined voltage between the working electrode 11 and the counter electrode 12, which voltage is selected so that chlorine dioxide is electrochemically converted at the working electrode 11. The working electrode 11 rests on the membrane 8 such that only a thin film of the inner electrolyte forms between the working electrode 11 and the membrane 8. This contributes to a rapid response time of the sensor 1.

The measurement circuit 13 is designed to detect a diffusion threshold current flowing through the inner electrolyte between the working electrode 11 and the counter electrode 12 given the applied voltage, and to generate a measurement signal based thereupon and output said measurement signal to the superordinate sensor electronics 3. Since, as described further above, the chlorine dioxide concentration that is present in the inner electrolyte is, in equilibrium, a measure of the chlorine dioxide content of a measuring fluid in contact with the membrane 8, the measurement current flowing between working electrode 11 and counter electrode 12 is, for its part, a measure of the chlorine dioxide content of the measuring fluid. The sensor electronics 3 may therefore determine and output a measurement value based on the measurement signal received by the measurement circuit 13, possibly using a calculation rule predetermined via calibration.

Figure 2:
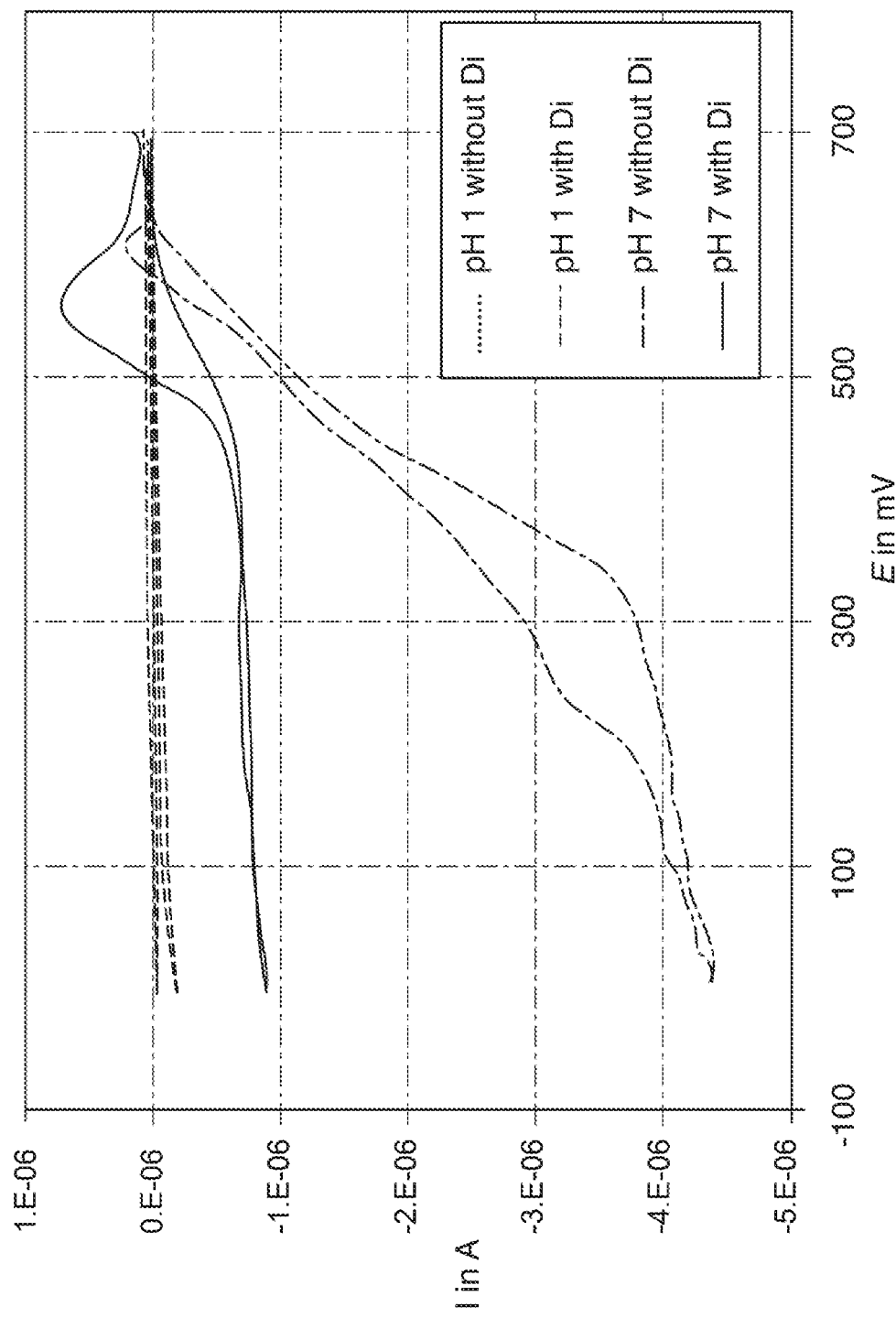
FIG. 2 shows a cyclic voltammograms detected with inner electrolytes of different compositions.

It could be experimentally determined that different electrochemical processes proceed at the negatively polarized working electrode 11 (cathode) depending on the pH value of the inner electrolyte. Shown in FIG. 2 are four cyclic voltammograms that were respectively recorded with a gold working electrode and a silver/silver chloride reference electrode in four electrolyte solutions of different composition. The electrolyte solutions are aqueous KCl solutions and differ with regard to their chlorine dioxide content and their pH value. A first cyclic voltammogram (dotted line, "pH 1 without Di") was recorded in a chlorine dioxide-free electrolyte with pH value 1. A second cyclic voltammogram (small dashed line; "pH 1 with Di") was recorded in the same electrolyte as the first cyclic voltammogram, with the addition of a predetermined chlorine dioxide concentration. A third cyclic voltammogram (large dotted line, "pH 7 without Di") was recorded in a chlorine dioxide-free electrolyte with pH value 7. A fourth cyclic voltammogram (solid line; "pH 7 with Di") was recorded in the same electrolyte as the third cyclic voltammogram, with the addition of a predetermined chlorine dioxide concentration. The chlorine dioxide concentration in the electrolyte used for the second cyclic voltammogram and in the electrolyte used for the fourth cyclic voltammogram is the same. The cyclic voltammograms recorded in the chlorine dioxide-free electrolytes show essentially the same behavior: a zero current results that shows no pH value dependency. The second and fourth cyclic voltammogram respectively show a current flow as of 400 mV and at lower potentials, which current flow is associated with the reduction of chlorine dioxide at the working electrode. It can be seen very distinctly that the current flowing in this potential range at a pH value of 1 is significantly greater than, namely approximately 5 times as large as, the current detected at a pH value of 7, although the chlorine dioxide concentration in both electrolytes is the same.

The observation made given the described cyclic voltammetric experiments may be interpreted as follows. Given a neutral pH value of the electrolyte and a voltage of 100 to 400 mV applied between working electrode and counter electrode, the following reaction proceeds vs. Ag/AgCl:

meaning that chlorine dioxide is reduced to chlorite with uptake of an electron.

Given acidic pH value of the inner electrolyte, chlorine dioxide is reduced to chloride at the cathode in a multistage reaction according to the following reaction equation with uptake of 5 electrons:

One possible explanation arises from the consideration of complex reaction equilibriums occurring in the acidic solution of chlorine dioxide.

For example, chlorite (ClO$_2$—) contained in the inner electrolyte in addition to chlorine dioxide may lead to the formation of chlorine radicals in the presence of chloride ions in the acidic pH value range:

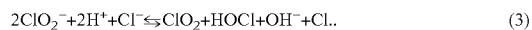

The chlorine radicals may further react to form chlorine, or with chlorite may also form hypochlorite:

Additional equilibriums known from the literature that possibly play a role at low pH values are reflected by the following reaction equations:

$$2ClO_2 + 2Cl^- \leftrightharpoons 2ClO_2^- + Cl_2, \quad (5)$$

$$2ClO_2 + H_2O \leftrightharpoons HClO_2 + HClO_3, \quad (6)$$

$$2HClO_3 + 2HCl \leftrightharpoons 2ClO_2 + Cl_2 + 2H_2O, \quad (7)$$

$$3HClO_3 \leftrightharpoons 2ClO_2 + HClO_4 + H_2O, \text{ and} \quad (8)$$

$$6ClO_2 + 3H_2O \leftrightharpoons HCl + 5HClO_3. \quad (9)$$

It results from this that, upon the pH value of an initially neutral inner electrolyte dropping into the acid pH range, the reaction (2) now proceeds at the working electrode instead of reaction (1) specified above. At the same time, chlorine, among other things, forms in the acidic pH range according to the equilibriums specified above, which chlorine may in turn react further to form HOCl. These are likewise electrochemically converted at the working electrode 11 given the voltage applied between working electrode and counter electrode for $ClO_2$ measurement. Using the calculation rule determined via calibration in the neutral pH range, adulterated measurement values thus already result due to the change of the electrode reaction of the chlorine dioxide. The final and intermediate products, in particular Cl2 and HOCl, that are formed according to the additional equilibriums (3)-(9) may further adulterate the measurement results obtained by means of the sensor. The additionally occurring reactions may also influence the response time of the sensor 1.

Given use of the sensor 1 in an acid measuring fluid, in addition to the chlorine dioxide analyte, additional components of the measuring fluid, in particular hydronium ions, may also get into the inner electrolyte. For example, this may occur via the membrane 8 if it allows the passage of water into the housing chamber 9. Even if the membrane 8 is designed to be hydrophobic or super-hydrophobic, and thus the diffusion of water across the membrane 8 into the inner electrolyte is largely or even entirely avoided, measuring fluid may penetrate into the housing chamber 9 via leaks in the probe housing 4 or the membrane 8. If the measuring fluid contains hydrochloric acid, gaseous hydrogen chloride together with chlorine dioxide may get into the inner electrolyte through the pores of even a super-hydrophobic membrane. All of these and additional processes may lead to a change, in particular to the decrease of the pH value of the inner electrolyte.

If pH values are too high, on the other hand, a disproportionation of the chlorine dioxide occurs according to the following equation:

$$2ClO_2 + 2OH^- \leftrightharpoons ClO_3^- + ClO_2^- + H_2O. \quad (10)$$

High pH values in the inner electrolyte are thus likewise to be avoided.

In the present example, the pH value of the inner electrolyte is therefore adjusted by means of a pH buffer to a value between 3.5 and 9, so that it is ensured on the one hand that an electrochemical conversion of the chlorine dioxide according to reaction equation (1) occurs stably at the working electrode 11, and on the other hand no disproportionation of chlorine dioxide according to reaction equation (10) occurs. The adjustment to a value of 7 or nearly 7, for example a value between the pH values of 5 and 8, has proven to be particularly advantageous. In the present example, the inner electrolyte is a solution based on water as solvent that, in addition to an electrolyte salt, for example potassium chloride, contains a technical phosphate buffer that keeps the pH value of the inner electrolyte stable at a predetermined pH value of 7.

The person skilled in the art knows a multitude of additional buffer systems by means of which the pH value of an aqueous electrolyte solution may be adjusted to a desired pH value in the range between 3.5 and 9, preferably between 5 and 8, and that may be used according to the present disclosure to stabilize the pH value of the inner electrolyte in an amperometric chlorine dioxide sensor.

The invention claimed is:

1. An amperometric sensor for determining measurement values of a measurand representing a chlorine dioxide content of a measuring fluid, comprising:
   a sensor housing defining a housing chamber;
   a membrane sealing the housing chamber at a distal end of the housing;
   a working electrode arranged within the housing chamber;
   a counter electrode arranged within the housing chamber, wherein the counter electrode is a silver electrode having a silver halide layer;
   an inner electrolyte contained in the housing chamber and contacting with the membrane, the working electrode and the counter electrode, wherein the inner electrolyte has a pH value between 3.5 and 9, inclusive, and includes a pH buffer formulated to stabilize the pH value of the inner electrolyte; and
   a measurement circuit electrically connected with the working electrode and the counter electrode and configured to apply a predetermined, constant voltage between the working electrode and the counter electrode and to generate a measurement signal representing a measurement value of the measurand using a current flowing through the electrolyte between the working electrode and the counter electrode given the predetermined voltage.

2. The amperometric sensor of claim 1, wherein the working electrode comprises a noble metal.

3. The amperometric sensor of claim 2, wherein the noble metal is gold.

4. The amperometric sensor of claim 1, wherein the pH buffer is a non-oxidizable buffer.

5. The amperometric sensor of claim 4, wherein the pH buffer is an inorganic buffer.

6. The amperometric sensor of claim 1, wherein the inner electrolyte is an aqueous solution that further includes at least one electrolyte salt.

7. The amperometric sensor of claim 1, wherein the membrane is permeable to chlorine dioxide.

* * * * *